United States Patent

Ogama

[11] Patent Number: 6,083,253
[45] Date of Patent: Jul. 4, 2000

[54] SKIN-CONTACT TYPE MEDICAL TREATMENT APPARATUS

[76] Inventor: Kenji Ogama, 3-42-11 Jingumae, Shibuya-ku, Tokyo, Japan

[21] Appl. No.: 09/102,894

[22] Filed: Jun. 23, 1998

[30] Foreign Application Priority Data

Jun. 26, 1997 [JP] Japan ...................... 9-170272

[51] Int. Cl.⁷ .................................................. A61N 1/04
[52] U.S. Cl. ................ 607/75; 607/2; 607/115; 600/372; 600/393
[58] Field of Search .................... 607/1, 2, 115, 607/149, 152, 153, 36, 37, 46, 48, 50, 75; 600/372, 382, 384, 386, 391, 393, 395; 606/32, 41; 604/20

[56] References Cited

U.S. PATENT DOCUMENTS

| | | | |
|---|---|---|---|
| 4,837,049 | 6/1989 | Byers et al. | 600/377 |
| 5,607,453 | 3/1997 | Ishiguro et al. | 607/2 |
| 5,772,688 | 6/1998 | Muroki | 607/1 |
| 5,848,095 | 12/1998 | Muroki | 607/72 |

FOREIGN PATENT DOCUMENTS

| | | |
|---|---|---|
| 61-55979 | 11/1986 | Japan . |
| 61-55980 | 11/1986 | Japan . |
| 62-32944 | 7/1987 | Japan . |
| 3-50927 | 10/1991 | Japan . |
| 8-173554 | 7/1996 | Japan . |

*Primary Examiner*—Kennedy J. Schaetzle
*Attorney, Agent, or Firm*—Kanesaka & Takeuchi

[57] ABSTRACT

A skin-contact type medical apparatus is formed of a first element for forming a pedestal, a protective resistance element attached to the first element, and a second element formed of an n-type semiconductor element and attached on one end of the protective resistance element away from the first element. The first element has a skin-contacting surface and a concave portion opened at a side of the skin-contacting surface to receive the protective resistance element. The protective resistance element has an elongated shape and a voltage controlling function. When the apparatus contacts the skin, the first and second elements serve as positive and negative electrodes, respectively, and the second element is electrically connected to the first element through the protective resistance element.

12 Claims, 3 Drawing Sheets

SKIN-CONTACT TYPE MEDICAL TREATMENT APPARATUS

BACKGROUND OF THE INVENTION

1. Field of the Invention

This invention relates to a medical treatment apparatus to be attached to the skin for regaining health, and more particularly to a skin-contact type medical treatment apparatus effective in the treatment of unidentified complaint syndrome such as muscular stiffness.

2. Description of the Prior Art

As a domestic treatment apparatus for alleviating muscular stiffness or aches of the shoulders or other parts of the body, there have so far been proposed ion-permeating devices for curing muscular or nervous fatigue by imparting, to the skin, electric stimulation brought about by electromotive force generated by a biogalvanic battery formed with the application of a weak direct current to the body (cf. Japanese Patent Publication Gazettes Nos. SHO 61-55979, SHO 61-55980 and SHO 62-32944, and Japanese Utility Model Publication Gazette No. 3-50927).

The aforementioned ion-permeating device is used in such a manner that a semiconducting crystal electrode and a metal electrode higher in standard single-electrode potential than the semiconducting crystal electrode are electrically connected to each other and brought into contact with the skin. The ion-permeating device enables muscular and nervous tissues to be continuously stimulated with electromotive force stably imparted to the skin through the electrodes without embrittling the electrodes during prolonged use. The ion-permeating device can achieve remarkably practical effects of treating the stiffness and aches in the body parts.

It seems that the function of alleviating such stiffness and aches in the body is fulfilled by electric stimulation caused by the biogalvanic battery. Thus, it is obvious that the medical effect of the ion-permeating device can be heightened by enlarging the current from the biogalvanic battery.

As it is, when the muscular and nervous tissues are physiologically activated by the biogalvanic battery, impedance in the skin between the electrodes of the biogalvanic battery is remarkably decreased. As a result, the current flowing in the skin is increased in quantity to impart an excessive stimulation to the skin tissues, thus possibly suffering skin damages.

For solving such a problem, there is proposed a skin-contact type medical treatment apparatus as shown in FIG. 6, in which a first element 11 serving as a metal positive electrode and a second element 12 serving as a semiconductor negative electrode are electrically connected through a protective resistance element 13 (Japanese Patent Application Public Disclosure No. HEI 8-173554(A)).

Now, the prior art skin-contact type medical treatment apparatus mentioned above will be described in further detail with reference to FIG. 6.

The first element 11 which is provided at its center with a protrusion is formed by plating a disk of copper with gold. This first element functions as a positive electrode of the biogalvanic battery when in contact with the skin. The second element 12 is made by oxidizing the surface of a zinc annular plate having a center hole so as form an n-type semiconductor of zinc oxide. This second element functions as a negative electrode when in contact with the skin. The protective resistance element 13 is made in such a manner that epoxy synthetic resin having carbon powder dispersed therein is uniformly applied to the surface (upper side in FIG. 6) of the first element 11 and dried to be formed into a resistance membrane. The protective resistance element 13 is adhered to the upper surface of the second element 12. An external circuit acting as the biogalvanic battery of the skin-contact type medical treatment apparatus is electrically connected to the protective resistance element 13.

Next, a method of producing the skin-contact type medical treatment apparatus will be explained.

First, the epoxy synthetic resin as the ingredient of the protective resistance element 13 is uniformly applied to the flat upper surface of the disk-shaped first element 11, and then, the second element 12 is placed on the flat upper surface of the first element before the epoxy synthetic resin becomes completely dry. Consequently, the first element 11 and second element 12 are superposed upon each other with the protective resistance element 13 interposed therebetween, with the center protrusion of the first element protruding upward through the center hole in the second element.

While the conventional skin-contact type medical treatment apparatus as shown in FIG. 6 brings about the intended effect of treating unidentified complaint syndrome such as shoulder or muscular stiffness and lumbago, it calls for the work of uniformly applying epoxy synthetic resin to form the protective resistance element in the manufacturing process. The work of producing the conventional apparatus requires not only much skill in uniformly applying the epoxy synthetic resin, but also much time and labor. Furthermore, the conventional apparatus is disadvantageous in that the method of manufacturing the apparatus becomes complicated, because of the processes of putting the second element on the first element and then drying the epoxy synthetic resin applied to the first element. Accordingly, the conventional apparatus entails the aforenoted serious problems so that the medical treatment apparatus can not be mass-produced uniformly in quality at a low cost with high efficiency.

OBJECT OF THE INVENTION

An object of the present invention is to provide a skin-contact type medical treatment apparatus having uniform quality and capable of being mass-produced at a low cost without requiring special skills in manufacture.

SUMMARY OF THE INVENTION

To attain the object described above according to the present invention, there is provided a skin-contact type medical treatment apparatus comprising a first element of metal serving as a positive electrode, a second element of an n-type semiconductor element serving as a negative electrode, and a protective resistance element having a voltage controlling function, through which the first and second elements are electrically connected. The first element is formed of a pedestal having a concave portion. The concave portion is made in the form of an opening in the skin-contacting side of the first element to be in contact with the skin. The protective resistance element is formed in the shape of a rod and placed in the concave portion of the first element in its standing posture.

The aforementioned second element comprises a skin-contact counterpart disposed on the skin-contact end part of the protective resistance element at which the protective resistance element comes into contact with the skin, and a basal counterpart disposed on the end opposite to the skin-contact end part of the protective resistance element. The skin-contact counterpart and basal counterpart of the second element are integrally united to the protective resistance element.

Since the works of joining the elements and drying the protective resistance element are not required for manufacturing the medical treatment apparatus of the present invention, the manufacturing process for the medical treatment apparatus can be simplified and carried out easily without requiring special skills. Consequently, the apparatus of the invention can be easily and speedily assembled and produced at a low cost and uniformly in quality with high efficiency.

Other and further objects of this invention will become obvious upon an understanding of the illustrative embodiments about to be described or indicated in the appended claims, and various advantages not referred to herein will occur to one skilled in the art upon employment of the invention in practice.

DESCRIPTION OF THE PREFERRED EMBODIMENTS

Figure 1:
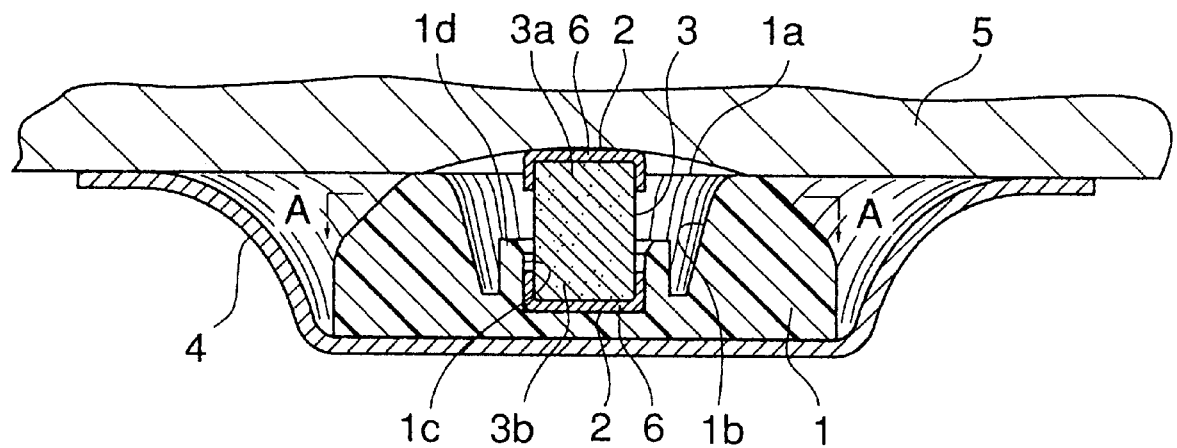
FIG. 1 is a sectional view showing a skin-contact type medical treatment apparatus in use according to this invention.
Figure 2:
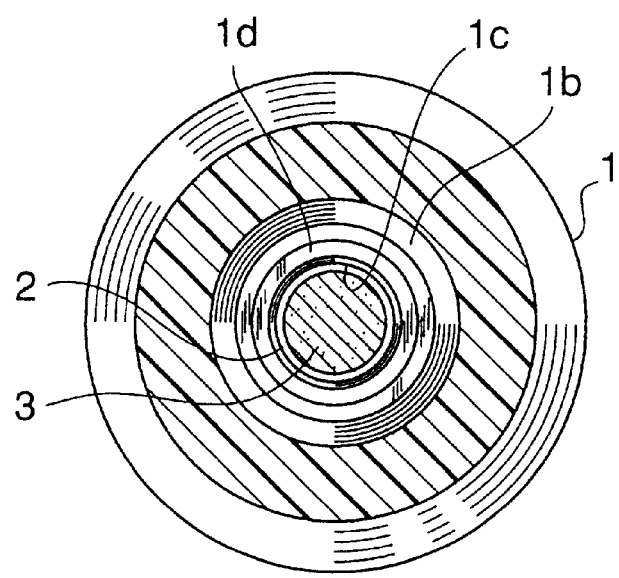
FIG. 2 is a sectional view taken along line A—A in FIG. 1.

One embodiment of the skin-contact type medical treatment apparatus according to the present invention will be described hereinafter with reference to FIG. 1 through FIG. 4.

The illustrated skin-contact type medical treatment apparatus comprises a pedestal 1 as a first element, a second element 2, and a protective resistance element 3 integrally connected to the second element 2.

The pedestal 1 of the first element functions as a positive electrode of a biogalvanic battery when coming into contact with the skin, and has its main body molded of synthetic resin. The exterior surface of the synthetic resin pedestal 1 is entirely plated with noble metals such as gold and platinum or other metal alloys to have electrical conductivity. The pedestal 1 has a concave portion 1b which is made in the form of an opening in the skin-contacting surface 1a to be in contact with the skin. The pedestal 1 is provided in its inner bottom with a support hole 1c for supporting the protective resistance element 3. In the embodiment shown in FIG. 1, a support frame 1d inside which the support hole 1c is bored is formed within the concave portion 1b.

As another possible way for making the pedestal 1 electrically conductive, the exterior surface of the pedestal may be plated with conductive metal higher in standard single-electrode potential than a semiconducting crystal electrode. The material with which the pedestal is plated is by no means limited to the gold, platinum and other metal alloys.

The second element 2 at a skin side is made of an n-type semiconductor element and serves as a negative electrode of the biogalvanic battery when being in contact with the skin.

Figure 3:
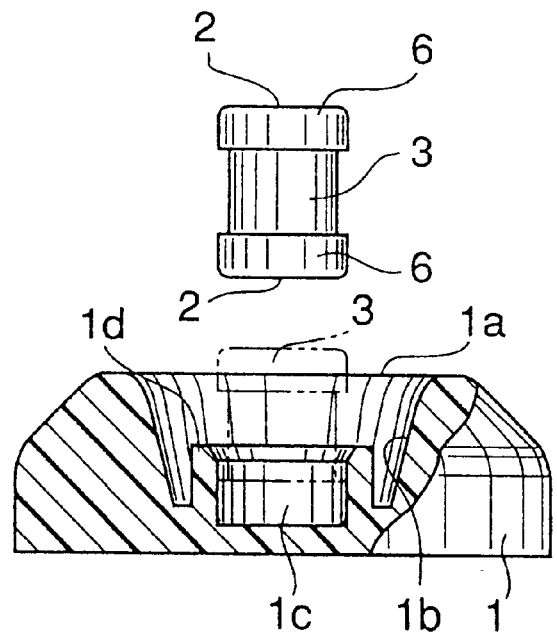
FIG. 3 is a partial cutaway front view showing the medical treatment apparatus of the invention in the exploded state.

The protective resistance element 3 is formed of a ceramic rod protruding upward, so that one end 3a (upper extremity in FIG. 1) of the rod produces a pointillage effect when bringing the protective resistance element 3 into press contact with the skin 5, as described later. The ceramic rod of the protective resistance element 3 in the embodiment shown in FIG. 1 and FIG. 3 is entirely coated with carbon and provided on both ends with conductive caps 6 (e.g. galvanized iron caps).

Onto the conductive caps 6 disposed on both ends of the protective resistance element 3, there are attached a skin-contact counterpart and a basal counterpart, which constitute the second element 2, respectively. The second element 2 is made by plating the conductive caps 6 with zinc to form galvanized surfaces, and then, treating the galvanized surfaces of the caps with acid or heat to form oxide semiconductor layers in the caps.

The protective resistance element 3 having a skin-contact end part 3a and a basal end part 3b covered with the conductive caps 6 in which n-type semiconductor elements are formed is similar in structure to a resistor usually used as an electronic part, for example. That is, the protective resistance element in this embodiment is equivalent in structure to a cap-shaped resistance element of zinc oxide. Accordingly, the second element 2 integrally connected to the protective resistance element 3 can be mass-produced at a low cost.

The protective resistance element 3 is placed in the concave portion 1b in the pedestal 1 in its standing posture, and securely held by tightly fitting the basal end part (lower part) 3b opposite to the skin-contact end part of the protective resistance element 3 into the support hole 1c formed in the concave portion 1b. Thus, the second element 2 placed on the basal end part 3b is in contact with the pedestal 1. Consequently, the second element 2 at the part 3a serves as the negative electrode of the n-type semiconductor element and is electrically connected to the pedestal 1 serving as the positive electrode through the protective resistance element 3 integrally connected to the second element.

The skin-contact type medical treatment apparatus of the invention is produced by forcibly inserting the basal end part of the protective resistance element 3 into the support hole 1c formed in the concave portion of the pedestal 1 with its skin-contacting surface 1a upward.

The skin-contact type medical treatment apparatus having the aforementioned structure in use is attached to a body part suffering stiffness or aches by use of adhesive cloth 4, as shown in FIG. 1 by way of example. At the time when the apparatus is attached to the skin, the skin-contact end part (upper part in FIG. 1) 3a of the rod-shaped protective resistance element 3 is brought in press contact with the skin by forcibly pressing the skin-contacting surface 1a of the pedestal 1 against the skin 5, thus to achieve the pointillage effect.

Figure 4:
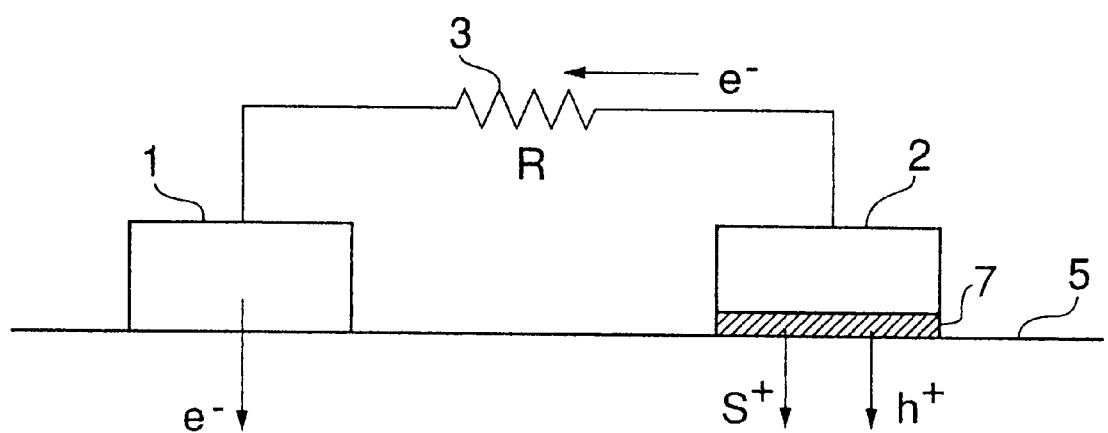
FIG. 4 is an explanatory diagram showing the operating principle of the medical treatment apparatus of the invention.

Next, the principle of treating unidentified complaint syndrome such as muscular stiffness by use of the skin-contact type medical treatment apparatus of the invention will be described with reference to FIG. 4.

Electrons $e^-$ which are emitted from the second element 2 at the part 3a of the n-type semiconductor element into the pedestal 1 through a resistance R (protective resistance element 3) are released into the skin 5, consequently bringing about a reduction effect.

On the other hand, the second element 2 at the part 3a of the n-type semiconductor element which is lacking the electrons $e^-$ produces holes $h^+$ which concentrate in the skin due to an internal electric field of a Schottky barrier generated in the surface layer of the second element being in contact with the skin. As a result, the n-type semiconductor element is ionized to allow the holes to permeate the skin along with positive ions $S^+$ due to the internal electric field. Consequently, the skin undergoes an oxidizing action brought about by the holes. The oxidizing action is stably continued owing to the Schottky barrier formed in the surface layer of the second element being in contact with the skin, which functions to prevent electrons and positive ions from flowing from the skin into the second element, while generating electromotive force for a long time. Reference numeral 7 denotes a high electrical field region.

The support hole 1c formed in the support frame 1d in the embodiment of FIG. 1 is elastically deformed when fitting the protective resistance element 3 thereinto, so that the protective resistance element 3 can be inserted into the support hole by a small force. Thus, the medical treatment apparatus of the invention can be easily assembled.

It is not always necessary to provide the pedestal 1 with the support frame 1d for holding the protective resistance element 3. The protective resistance element 3 may be retained within the support hole 1c, but not necessarily supported by the support frame 1d. Also, the concave portion 1b should not be understood as being limited to a dent shape as illustrated and may be formed in a through hole piercing through the pedestal.

According to the foregoing embodiment, the skin-contact type medical treatment apparatus of the invention can be mass-produced at a low cost, as the synthetic resin pedestal used as the first element can be readily obtained by plating, and common resistance parts put on the market can be used instead of the protective resistance element integrally connected to the second element. Moreover, since there is no need for adhering and drying works for forming the protective resistance element, the medical treatment apparatus of the invention can be easily assembled by a simple operation without requiring special skills and produced uniformly in quality. Besides, the work of assembling the apparatus can be carried out simply and speedily. The protective resistance element shaped in a protrusion in the present apparatus brings about a pointillage effect and functions as the electrodes of the biogalvanic battery, protective resistor and short-circuit of an external circuit, resulting in simplicity in structure and high productivity of the skin-contact type medical treatment apparatus of the invention.

Figure 5:
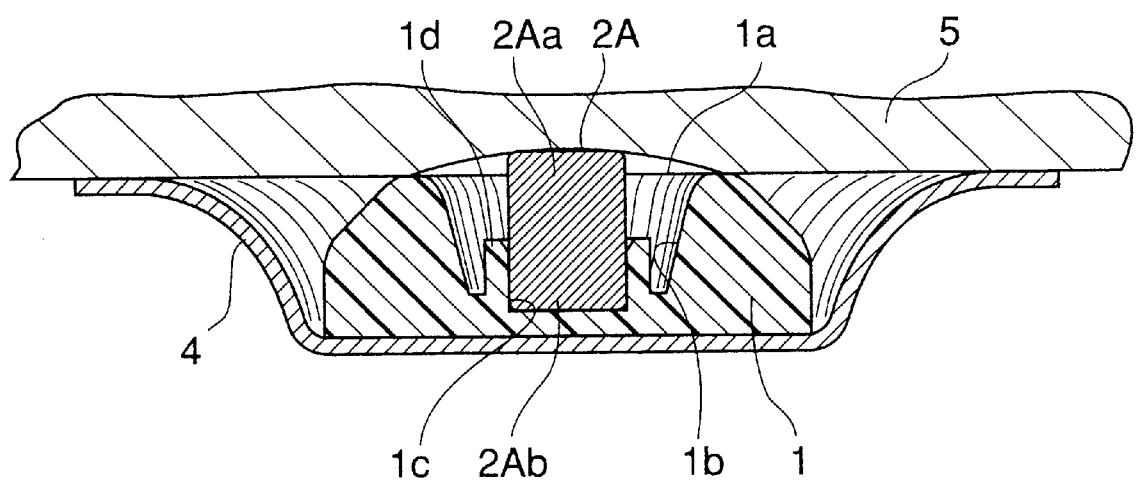
FIG. 5 is a sectional view of another embodiment of a skin-contact type medical treatment apparatus of the invention for showing a condition in use.
Figure 6:
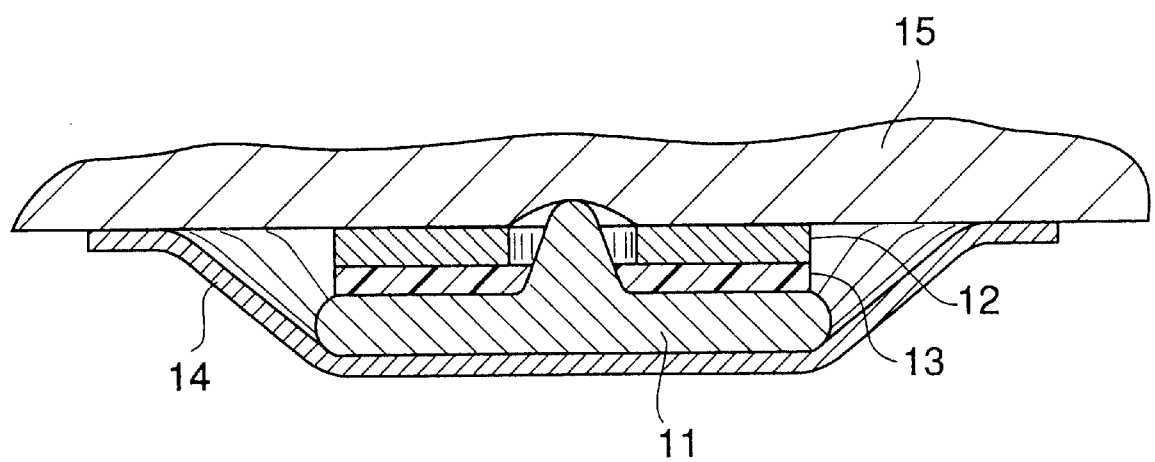
FIG. 6 is a sectional view of a conventional skin-contact medical treatment apparatus in use.

As another embodiment of the medical treatment apparatus of the invention, as shown in FIG. 5, an apparatus may be formed such that a pedestal 1 as a first element is made as a positive electrode, and a second element 2A which is formed of an n-type semiconductor element and to which a voltage control characteristic may be added is made as a negative electrode, both elements being electrically connected together. The medical treatment apparatus in this embodiment does not have a protective resistance element 3 like the embodiment shown in FIGS. 1–4, but this embodiment includes the first element, which is substantially the same as the first element 1 shown in FIG. 1.

The second element 2A is an oxide semiconductor element. The method of forming the second element 2A is explained. For example, a zinc plating is made on an entire surface of an iron rod, which is then subjected to acid or heat treatment. As a result, the outer surface of the iron rod becomes zinc oxide (ZnO), so that the second element 2A as the oxide semiconductor element is formed.

As another example for forming the second element, the iron rod may have a tin plating instead of the zinc plating, to thereby form tin oxide (SnO) on the surface of the iron rod. As a result, the second element as the oxide semiconductor element is formed. The oxide semiconductor element may be formed of, in addition to zinc oxide and tin oxide, for example, $In_2O_3$, $Sb_2O_5$, $Al_2O_{5-x}$, $VO_{5-x}$, and so on.

The second element 2A is placed in an concave portion 1b of the pedestal 1 in an upstanding condition. An end 2Ab at a lower side in FIG. 5 is held by being forcibly inserted into a support hole 1c of the concave portion 1b, and the end 2Ab contacts the pedestal 1. Therefore, the second element 2A, which becomes the negative electrode of the n-type semiconductor element, is electrically connected to the pedestal 1 forming the positive electrode. The upper end 2Aa of the second element 2A at the upper side in FIG. 5 becomes a projection providing a pointillage effect to the skin 5 at the time of skin contact.

The first element 1 as shown in FIGS. 1 and 5 is the pedestal 1 made of a synthetic resin, on an entire outer surface of which a metal plating by noble metal or alloy thereof is applied to thereby form an electro-conductivity element. However, the first element 1 may be a pedestal formed entirely of an electro-conductive material, such as noble metal and so on, and need not be limited to a member, an outer surface of which is covered by an electroconductive material.

It is to be understood that the invention is not limited in its application to the details of the construction and arrangement of the parts illustrated in the accompanying drawings, since the invention is capable of talking other embodiments and of being practiced or carried out in various ways. Also, it is to be understood that the phrases and terms employed herein are for the purpose of description and not of limitation.

What is claimed is:

1. A skin-contact type medical apparatus, comprising:
   a first element for forming a pedestal, said first element having a skin-contacting surface and a concave portion opened at a side of the skin-contacting surface, and serving as a positive electrode,
   a protective resistance element having an elongated shape and a voltage controlling function, said protective resistance element being disposed in the concave portion in an upstanding condition, and
   a second element formed of an n-type semiconductor element and attached on one end of the protective resistance element away from the first element, said second element operating as a negative electrode and being electrically connected to the first element through the protective resistance element.

2. A skin-contact type medical treatment apparatus as claimed in claim 1, wherein said pedestal of the first element is made of a synthetic resin and is plated with conductive metal higher in standard single-electrode potential than a semiconductor crystal of the n-type semiconductor.

3. A skin-contact type medical treatment apparatus as claimed in claim 2, wherein said pedestal of the first element is plated with metal selected from noble metal or an alloy thereof.

4. A skin-contact type medical treatment apparatus as claimed in claim 1, wherein said pedestal of the first element is provided in the concave portion with a support hole, into which an end of the protective resistance element is fitted.

5. A skin-contact type medical treatment apparatus as claimed in claim 1, wherein said second element is integrally formed with the protective resistance element.

6. A skin-contact type medical treatment apparatus as claimed in claim 1, wherein said protective resistance element includes electro-conductive caps at two ends, the second element being formed in each of said electro-conductive caps.

7. A skin-contact type medical treatment apparatus as claimed in claim 1, wherein said first element is formed of an electro-conductive material.

8. A skin-contact type medical apparatus, comprising:
   a first element for forming a pedestal made of a synthetic resin and plated with conductive metal higher in standard single-electrode potential than a semiconductor crystal of an n-type semiconductor element, said first element having a skin-contacting surface, a concave portion opened at a side of the skin-contacting surface and a support hole at a bottom of the concave portion, and serving as a positive electrode,
   a protective resistance element having an elongated shape with electro-conductive caps at two ends, and a voltage controlling function, one end of the protective resistance element being forcibly disposed in the support hole, and
   two second elements formed of an n-type semiconductor element and attached on opposite ends of the protective resistance element integrally with the electro-conductive caps, one of the second elements operating as a negative electrode and being electrically connected to the first element through the protective resistance element.

9. A skin-contact type medical apparatus, comprising:
   a first element for forming a pedestal and serving as a positive electrode, said first element having a skin-contacting surface and a concave portion opened at a side of the skin-contacting surface, and
   a second element operating as a negative electrode and electrically connected to the first element, said second element being formed of an n-type semiconductor element and having a voltage controlling function, said second element having an elongated shape and being held in the concave portion in an upstanding condition.

10. A skin-contact type medical treatment apparatus as claimed in claim 9, wherein said pedestal of the first element is made of a synthetic resin and is plated with conductive metal higher in standard single-electrode potential than a semiconductor crystal of the n-type semiconductor electrode.

11. A skin-contact type medical treatment apparatus as claimed in claim 9, wherein said pedestal of the first element is provided in the concave portion with a support hole, into which an end of the second element is fitted.

12. A skin-contact type medical treatment apparatus as claimed in claim 11, wherein said first element is formed of an electro-conductive material.

* * * * *